US00PP31114P2

(12) United States Plant Patent
Head et al.

(10) Patent No.: US PP31,114 P2
(45) Date of Patent: Nov. 26, 2019

(54) AZALEA PLANT NAMED 'RLH2-4P1-5'

(50) Latin Name: *Rhododendron hybrida*
Varietal Denomination: RLH2-4P1-5

(71) Applicants: Robert Harold Head, Seneca, SC (US); Lisa Jones Head, Seneca, SC (US)

(72) Inventors: Robert Harold Head, Seneca, SC (US); Lisa Jones Head, Seneca, SC (US)

(73) Assignee: HEAD'S SELECT, INC., Seneca, SC (US)

( * ) Notice: Subject to any disclaimer, the term of this patent is extended or adjusted under 35 U.S.C. 154(b) by 0 days.

(21) Appl. No.: 15/999,984

(22) Filed: Sep. 7, 2018

(51) Int. Cl.
*A01H 5/00* (2018.01)
*A01H 6/36* (2018.01)

(52) U.S. Cl.
USPC ..... Plt./239

(58) Field of Classification Search
USPC ..... Plt./238, 239
See application file for complete search history.

*Primary Examiner* — Susan McCormick Ewoldt
(74) *Attorney, Agent, or Firm* — C. A. Whealy

(57) ABSTRACT

A new and distinct cultivar of Azalea plant named 'RLH2-4P1-5', characterized by its compact, upright to outwardly spreading and mounding plant habit; vigorous growth habit and rapid growth rate; freely basal branching habit; dense and bushy appearance; relatively small and evergreen dark green-colored leaves that do not abscise during the winter; freely flowering habit with remontant flowering during the spring, summer and autumn; hose-in-hose to double hose-in-hose flowers that are light red purple in color with white-colored centers during the spring; and excellent garden performance and temperature tolerance.

3 Drawing Sheets

Botanical designation: *Rhododendron hybrida.*
Cultivar denomination: 'RLH2-4P1-5'.

BACKGROUND OF THE INVENTION

The present Invention relates to a new and distinct cultivar of Azalea plant, botanically known as *Rhododendron hybrida*, commercially referred to as an evergreen Azalea plant and hereinafter referred to by the name 'RLH2-4P1-5'.

The new Azalea plant is a product of a planned breeding program conducted by the Inventors in Long Creek, Oconee County, S.C. The objective of the breeding program is to create new compact evergreen Azalea plants having dense growth habit, good winter leaf retention, large attractive flowers, flowers with good temperature tolerance, consistent remontant flowering habit, good garden performance and low and high temperature tolerance.

The new Azalea plant originated from a cross-pollination made by the Inventors in 2010 in Long Creek, Oconee County, S.C., of a proprietary selection of *Rhododendron hybrida* identified as code number RLH-10.1036P1, not patented, as the female, or seed, parent with *Rhododendron hybrida* 'RLH1-5P1', disclosed in U.S. Plant Pat. No. 24,975, as the male, or pollen, parent. The new Azalea plant was discovered and selected by the Inventors as a single flowering plant within the progeny of the stated cross-pollination in a controlled greenhouse environment in Long Creek, Oconee County, S.C. in 2013.

Asexual reproduction of the new Azalea plant by semi-hardwood stem cuttings taken in a controlled greenhouse environment in Long Creek, Oconee County, S.C. since 2013 has shown that the unique features of this new Azalea plant are stable and reproduced true to type in successive generations.

SUMMARY OF THE INVENTION

Plants of the new Azalea have not been observed under all possible combinations of environmental conditions and cultural practices. The phenotype may vary somewhat with variations in environmental conditions such as temperature, daylength and light intensity without, however, any variance in genotype. The following traits have been repeatedly observed and are determined to be the unique characteristics of 'RLH2-4P1-5'. These characteristics in combination distinguish 'RLH2-4P1-5' as a new and distinct Azalea plant:

1. Compact, upright to outwardly spreading and mounding plant habit.
2. Vigorous growth habit and rapid growth rate.
3. Freely basal branching habit; dense and bushy appearance.
4. Relatively small and evergreen dark green-colored leaves that do not abscise during the winter.
5. Freely flowering habit with remontant flowering during the spring, summer and autumn.
6. Hose-in-hose to double hose-in-hose flowers that are light red purple in color with white-colored centers during the spring.
7. Excellent garden performance and temperature tolerance.

Plants of the new Azalea differ primarily from plants of the female parent selection in the following characteristics:

1. Plants of the new Azalea are more freely branching than plants of the female parent selection.
2. Plants of the new Azalea produce hose-in-hose to double hose-in-hose flowers whereas plants of the female parent selection produce semi-double flowers.

Plants of the new Azalea differ primarily from plants of the male parent, 'RLH1-5P1', in the following characteristics:

1. Plants of the new Azalea are more upright than and not as low spreading as plants of 'RLH1-5P1'.
2. Plants of the new Azalea produce hose-in-hose to double hose-in-hose flowers whereas plants of 'RLH1-5P1' produce semi-double flowers.
3. Plants of the new Azalea have larger flowers than plants of 'RLH1-5P1'.

Plants of the new Azalea can be compared to the plants of 'Robleg', disclosed in U.S. Plant Pat. No. 15,227. In side-by-side comparisons conducted by the Inventors in Long Creek, Oconee County, S.C., plants of the new Azalea differed primarily from plants of 'Robleg' in the following characteristics:

1. Plants of the new Azalea were more uniform in plant shape and required less pruning to maintain a more uniform shape than plants of 'Robleg'.
2. Plants of the new Azalea flowered in the spring, summer and autumn whereas plants of 'Robleg' flowered only in the spring and autumn.
3. Plants of the new Azalea produced hose-in-hose to double hose-in-hose flowers whereas plants of 'Robleg' produced single-type flowers.
4. Flower petals of plants of the new Azalea were more undulate and ruffled than flower petals of plants of 'Robleg'.
5. Plants of the new Azalea and 'Robleg' differed in flower color as plants of 'Robleg' had white-colored flowers.
6. Plants of the new Azalea were more cold hardy than plants of 'Robleg'.

BRIEF DESCRIPTION OF THE PHOTOGRAPHS

The accompanying colored photographs illustrate the overall appearance of the new Azalea plant showing the colors as true as it is reasonably possible to obtain in colored reproductions of this type. Colors in the photographs may differ slightly from the color values cited in the detailed botanical description which accurately describe the colors of the new Azalea plant.

The photograph on the first sheet is a side perspective view of a typical three-year old flowering plant of 'RLH2-3P8-2' grown during the spring.

The photograph on the second sheet is a side perspective view of a typical two-year old flowering plant of 'RLH2-3P8-2' grown during the spring.

The photograph on the third sheet is a close-up view of typical flowers of plants of 'RLH2-3P8-2' grown during the spring.

DETAILED BOTANICAL DESCRIPTION

The aforementioned photographs, following observations and measurements describe plants grown during the spring and early summer in three-gallon containers in El Campo and Fort Worth, Tex. and under cultural practices typical of commercial Azalea production. During the production of the plants, day temperatures averaged 24° C. and night temperatures averaged 14° C. Plants used for the detailed description were two years old. In the following description, color references are made to The Royal Horticultural Society Colour Chart, 2007 Edition, except where general terms of ordinary dictionary significance are used.

Botanical classification: *Rhododendron hybrida* 'RLH2-4P1-5'.

Commercial classification: Evergreen Azalea.

Parentage:

*Female, or seed, parent.*—Proprietary selection of *Rhododendron hybrida* identified as code number RLH-10.1036P1, not patented.

*Male, or pollen, parent.*—*Rhododendron hybrida* 'RLH1-5P1', disclosed in U.S. Plant Pat. No. 24,975.

Propagation:

*Type.*—By semi-hardwood stem cuttings.

*Time to initiate roots, summer.*—About 25 to 30 days at temperatures of 27° C. to 30° C.

*Time to initiate roots, winter.*—About 35 to 45 days at temperatures of 16° C. to 17° C.

*Time to produce a rooted young plant, summer.*—About 60 to 70 days at temperatures of 27° C. to 30° C.

*Time to produce a rooted young plant, winter.*—About 80 to 100 days at temperatures of 16° C. to 17° C.

*Root description.*—Fine, fibrous; initially white in color becoming light brown with development; actual color of the roots is dependent on substrate composition, water quality, fertilizer type and formulation, substrate temperature and physiological age of roots.

*Rooting habit.*—Freely branching; dense.

Plant description:

*Plant form, plant and growth habit.*—Perennial and evergreen flowering subshrub; tall, upright to outwardly spreading and mounding plant habit; vigorous growth habit; rapid growth rate; freely flowering habit with numerous hose-in-hose to double hose-in-hose flowers.

*Branching habit.*—Freely branching habit with lateral branches potentially developing at every node; dense and bushy appearance; pinching (removal of terminal apex) enhances lateral branch development.

*Plant height, soil level to top of flowers.*—About 53 cm.

*Plant diameter, area of spread.*—About 48 cm.

*Lateral branch description.*—Length: About 14 cm to 20 cm. Diameter at base: About 6 mm. Internode length at fully developed upper leaf axils: About 9 mm. Strength: Strong. Aspect: Upright to outwardly spreading. Texture and luster, developing: Pubescent, fine white- colored hairs; matte. Texture and luster, mature: Woody; pubescent, fine rusty brown-colored hairs; matte. Color, developing: Close to 146A to 146B. Color, semi-hardwood: Close to 146A to 146B becoming close to 165A with development. Color, mature: Close to 166A.

*Leaf description.*—Arrangement: Alternate; simple. Leaf retention: Very good winter leaf retention has been observed on plants of the new Azalea. Length: About 4.5 cm. Width: About 2.4 cm. Shape: Elliptic, obovate to oblanceolate. Apex: Acute; mucronulate. Base: Cuneate. Margin: Entire; ciliate. Venation pattern: Pinnate; reticulate. Texture, upper and lower surfaces: Sparsely pubescent; coriaceous, tough. Luster, upper surface: Glossy. Luster, lower surface: Slightly glossy. Color: Developing leaves, upper surface: More green than N137A to N137B. Developing leaves, lower surface: More green than 137B to 137C. Fully expanded leaves, upper surface:

Darker green than N137A; venation, close to 146A to 146B. Fully expanded leaves, lower surface: Close to 146B; venation, close to 146B to 146C. Petioles: Length: About 1 cm. Diameter: About 3 mm. Strength: Strong. Texture and luster, upper and lower surfaces: Pubescent; matte. Color, upper surface: Close to 146B. Color, lower surface: Close to 146B to 146C.

Flower description:

*Flower appearance and arrangement*.—Hose-in-hose to double hose-in-hose flowers arranged mostly outwardly in clusters at terminals and sub-terminals; two whorls with five petals each fused towards the base with some or all stamens transformed into petaloids.

*Natural flowering season*.—Spring, April to May, and then remontant flowering during the summer and autumn, July to October or until frost in USDA Hardiness Zone 6b.

*Flowering habit*.—Freely flowering habit with usually about three flowers per terminal or sub-terminal.

*Flower longevity*.—Flowers are durable and long-lasting; depending on the temperature, flowers last about ten days on the plant, dependent on ambient temperatures; flowers not persistent.

*Fragrance*.—None detected.

*Flower diameter*.—About 6.5 cm.

*Flower depth*.—About 3.5 cm.

*Flower buds* (*before showing color*).—Length: About 1.8 cm. Diameter: About 7 mm. Shape: Ovoid. Texture and luster: Pubescent, matte. Color: Close to 144A.

*Petals*.—Length, outer whorl: About 5 cm. Length, inner whorl: About 4.5 cm. Width, outer whorl: About 3 cm. Width, inner whorl: About 2.5 cm. Shape: Broadly ovate to obovate; roughly spatulate. Apex: Rotund or occasionally emarginate; undulate. Margin: Entire; undulate. Texture, upper and lower surfaces: Smooth, glabrous; rugulose; waxy to velvety in appearance. Color: When opening and fully opened, upper surface: Distally, close to 58A; proximally, close to 62C to 62D. When opening and fully opened, lower surface: Distally, close to 58A to 58B; proximally, close to 62D.

*Petaloids*.—Quantity and appearance: If present, about one to three per flower; irregular in shape and size. Apex: Rotund or occasionally emarginate; undulate. Margin: Entire; undulate. Texture, upper and lower surfaces: Smooth, glabrous; rugulose; waxy to velvety in appearance. Color: When opening and fully opened, upper surface: Distally, close to 58A; proximally, close to 62C to 62D. When opening and fully opened, lower surface: Distally, close to 58A to 58B; proximally, close to 62D.

*Sepals*.—Arrangement: Five in a single whorl, fused at the base forming a campanulate to star-shaped corona. Length: About 5 mm. Width: About 3 mm. Shape: Lanceolate. Apex: Acute. Base: Fused. Margin: Entire; ciliate. Texture and luster, upper and lower surfaces: Densely pubescent; matte. Color, upper and lower surfaces: Close to 144A to 144B.

*Peduncles*.—Length: About 1 cm. Diameter: About 2.5 mm. Angle: Upright to outwardly. Strength: Strong; flexible. Texture and luster: Pubescent; matte. Color: Close to 144B to 144C.

*Reproductive organs*.—Androecium: Quantity of stamens per flower: If present, up to five; may be transformed into petaloids. Filament length: About 2.7 cm to 3.2 cm. Filament color: Close to NN155A. Anther shape: Porandrous with two oblong, tubular to lunate-shaped pollen sacks basifixed to the filament. Anther length: About 3 mm. Anther color: Close to 175B. Pollen amount: None observed. Gynoecium: Pistil length: About 4.6 cm. Stigma shape: Round to flattened (capitate). Stigma color: Close to 59A. Style length: About 4 cm. Style color: Close to NN155A. Ovary color: Close to 146A.

*Fruits and seeds*.—Fruit and seed development have not been observed on plants of the new Azalea to date.

Garden performance & temperature tolerance: Plants of the new Azalea have been observed to be very tolerant to rain, wind and temperatures ranging from about −22° C. to 45° C. Plants of the new Azalea are adaptable for USDA Hardiness Zones 6B to 9.

Disease & pest resistance: Plants have not been observed to be resistant to pathogens and pests common to Azalea plants to date.

It is claimed:

1. A new and distinct cultivar of Azalea plant named 'RLH2-4P1-5' as illustrated and described.

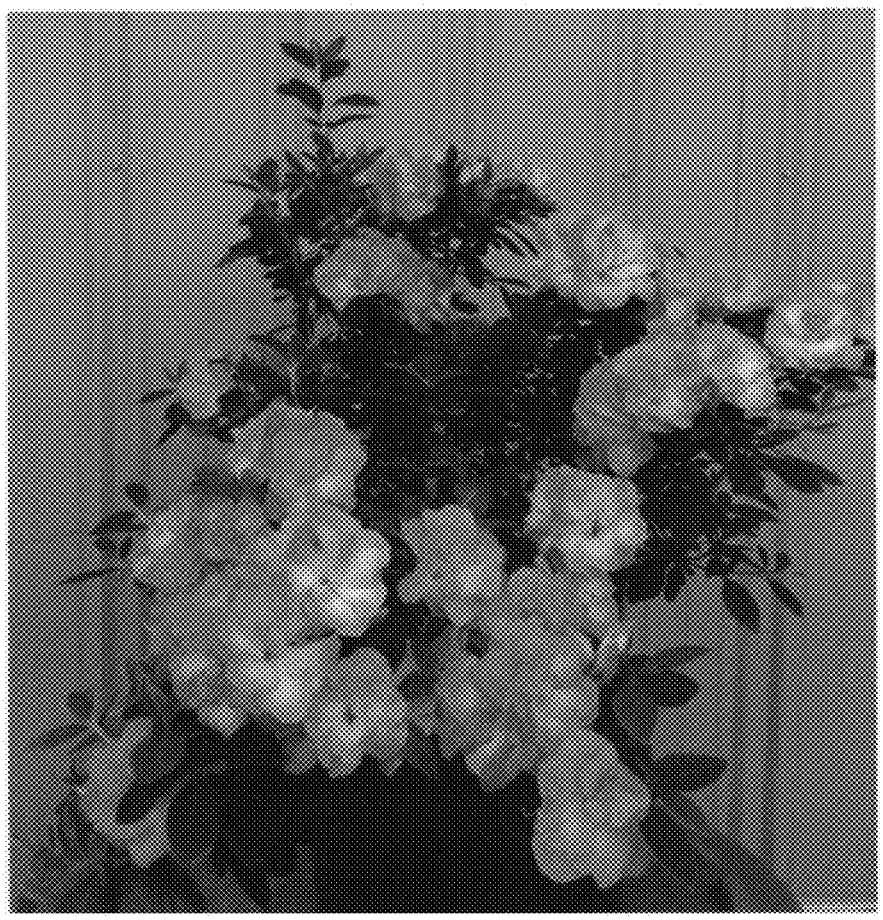

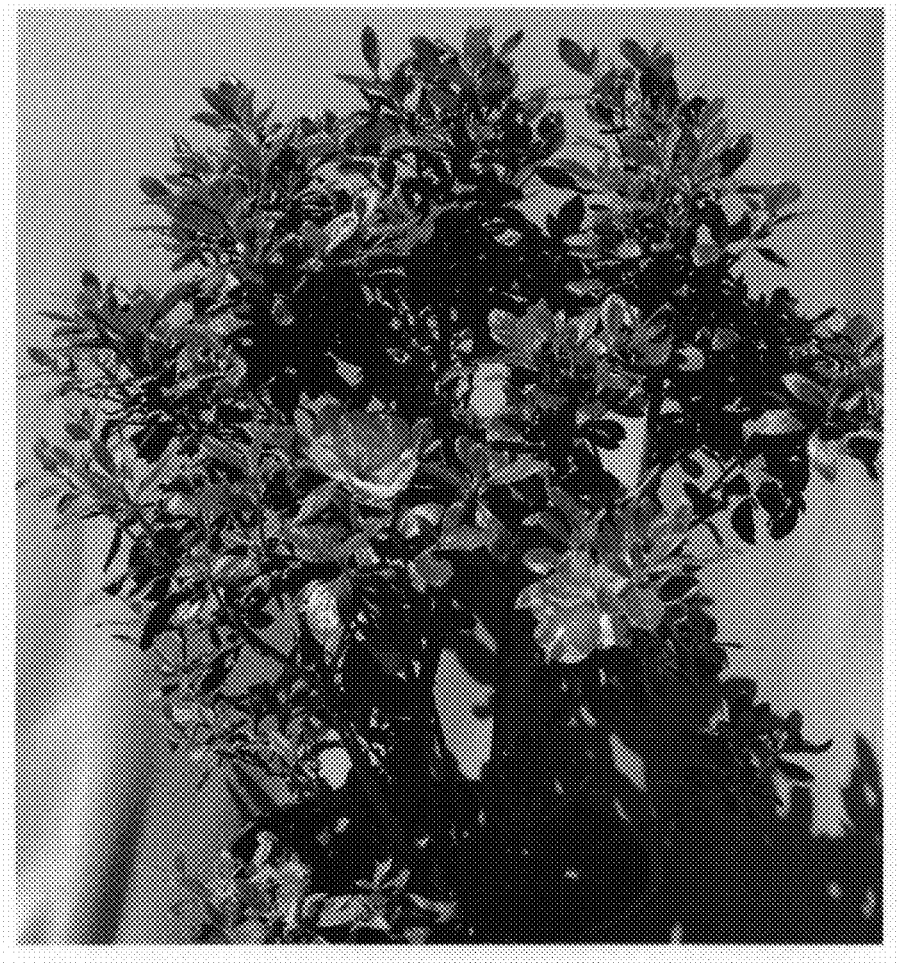

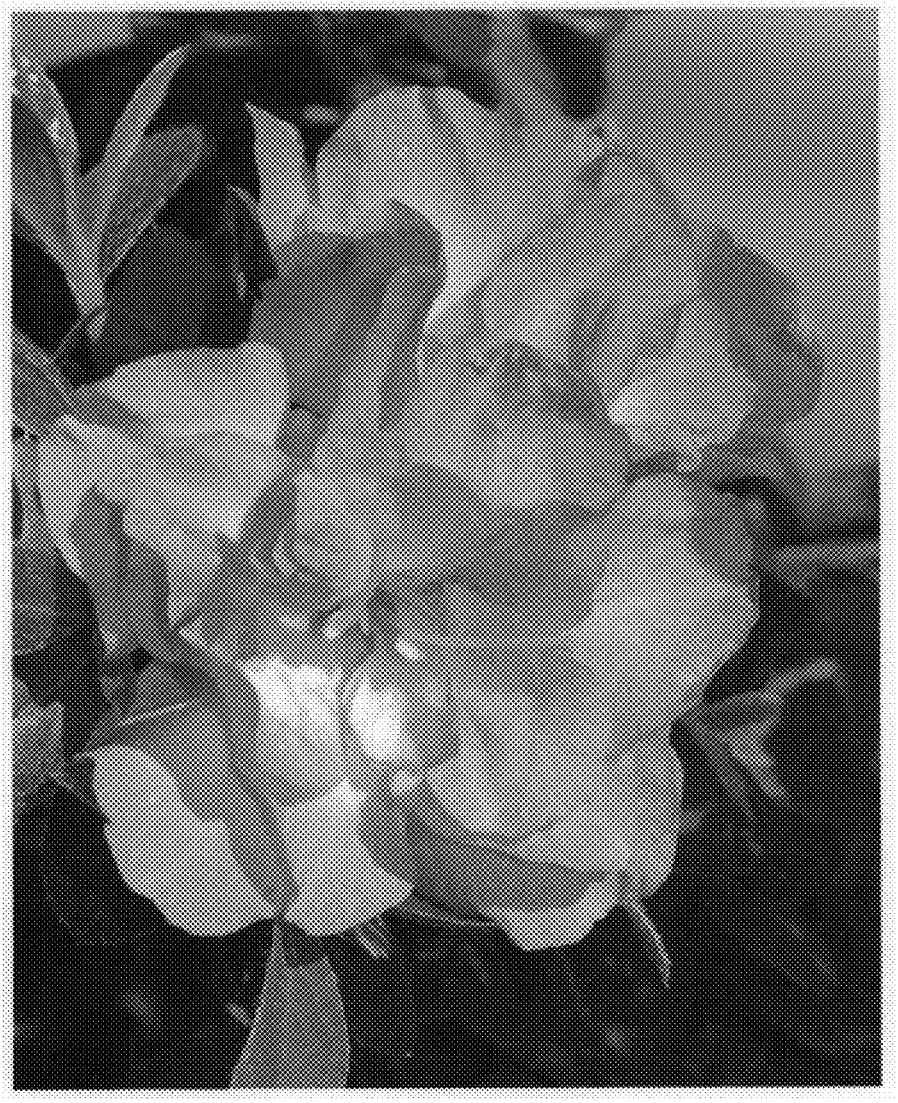

* * * * *